United States Patent [19]

Tonucci et al.

[11] Patent Number: 5,234,594
[45] Date of Patent: Aug. 10, 1993

[54] NANOCHANNEL FILTER

[75] Inventors: Ronald J. Tonucci, Temple Hills, Md.; Brian L. Justus, Springfield, Va.

[73] Assignee: The United States of America as represented by the Secretary of the Navy, Washington, D.C.

[21] Appl. No.: 897,628

[22] Filed: Jun. 12, 1992

[51] Int. Cl.⁵ ............................................. B01D 71/04
[52] U.S. Cl. ............................ 210/500.26; 210/510.1
[58] Field of Search ............... 210/500.26, 496, 510.1; 264/49

[56] References Cited

U.S. PATENT DOCUMENTS

| 4,101,130 | 7/1978 | Balkwill | 65/31 |
| 4,912,531 | 3/1990 | Reef et al. | 357/12 |
| 4,923,608 | 5/1990 | Flottmann et al. | 210/500.26 X |
| 5,059,001 | 10/1991 | Shimizu | 359/24 |

OTHER PUBLICATIONS

Kraus, et al., "Salt Rejection by a Porous Glass", from Science, vol. 151, pp. 194–195, Jan. 1966.

Primary Examiner—Frank Spear
Attorney, Agent, or Firm—Thomas E. McDonnell; George A. Kap

[57] ABSTRACT

The present invention provides a wafer-like glass filter having channels therethrough having an average diameter of less than 1 micron, and further provides methods of making the filter.

11 Claims, 7 Drawing Sheets

NANOCHANNEL FILTER

BACKGROUND OF THE INVENTION

1. Field of the Invention

The present invention relates to a filer for ultrafiltration.

2. Prior Art

For particles, whose average dimensions are less than 2 microns, there are essentially three methods readily available to efficiently separate or filter particles by size. Processing times are usually measured in hours and sample volumes to be separated are typically a very small fraction of a milliliter. They generally involve the use of a supporting medium, where particles are easily trapped and recovery of all starting materials is often difficult if not impossible.

Filtration of particles on the order of tens or hundreds of Angstroms by size is frequently referred to as Molecular Filtration or Ultrafiltration. The filters with the highest selectivity or sharpest cutoff in particle size, are composed of thin semipermeable membranes made from a variety of polymer materials. These membranes are anisotropic or asymmetric in cross section and may not be used at temperatures above 35° C. A model membrane molecular filtration system consisting of uniform pores, and a solid spherical solute 20% as large as the pore will theoretically pass only 85% of the solute, the remainder being retained within the membrane. The resulting filtrate will be only partially fractionated. Efficient particle size separation between two narrow size distributions using membrane molecular filtration often requires size differentials of over an order of magnitude.

The best filtration rate of membranes at 50 PSI is typically about 0.1 ml/min/cm$^2$ for particles on the order of 100's of Angstroms in diameter. However, membranes are themselves pressure sensitive and consideration has to be given to the advantages of increased flux as the pressure is increased versus membrane compression which skews the effective filtration diameter of the filter.

Control pore filter glasses are made with nominal pore sizes as small as 7.5 nanometers. The pores are randomly oriented within the glass particles and have typical pore size distributions of approximately 10%. The glass particles are typically 50–500 microns in size and are themselves randomly oriented when packed into filter columns. The pores are therefore randomly oriented across the pressure gradient of the filter column, broadening the dispersion for identical materials transport and lowering the resolution of this filtering system. In addition, material may flow around the voids surrounding the individual glass particles composing the column, further reducing the filtering resolution. To make up for these deficiencies, the length of the filtering column must usually be considerably extended.

Gel permeation chromatography can be used as a very sensitive method to separate particles of different size for certain ranges of particle size distributions, around room temperature. The gel acts as a supporting medium for the transport of materials and generally retains the majority of the smaller particles. If the separated particles are to be collected, the medium must eventually be removed from the material of interest. This can be a very difficult and laborious procedure.

SUMMARY OF THE INVENTION

In one embodiment, the present invention provides a wafer-like glass filter having substantially identical channels therethrough having an average diameter of less than 1 micron.

In another embodiment, the present invention provides a method for forming such a filter comprising the steps of:

inserting acid etchable glass rods into respective inert hollow glass tubes;

heating the rods and tubes to fuse each respective rod to a respective tube;

drawing each of the fused rods and tubes to reduce the diameter of the rods and tubes to thereby form a filament;

stacking a plurality of the filaments together to form a stack of filaments;

heating the stack of filaments to fuse the filaments together to form an elongated bar having a plurality of channels filled with etchable glass;

drawing the bar until each of the channels has a diameter of less than 1 micron;

cutting the elongated bar to form a wafer-like filter;

annealing the filter at an elevated temperature; and acid etching the etchable glass in the wafer-like filter to form channels therethrough having an average diameter of less than about 1 micron.

In another embodiment, the present invention provides a method for forming a filter comprising the steps of:

stacking acid etchable glass filaments with acid inert glass filaments to form a stack of filament rods having an oriented array of acid etchable glass filaments;

heating the stack of filaments to fuse the filaments together to form an elongated bar having a plurality of channels filled with etchable glass;

drawing said bar until each of the channels has a diameter of less than 1 micron;

cutting the elongated bar to form a wafer-like filter;

annealing the filter at an elevated temperature; and acid etching the etchable glass in the wafer-like filter to form channels therethrough having an average diameter of less than about 1 micron.

DETAILED DESCRIPTION OF THE INVENTION

Figure 1:
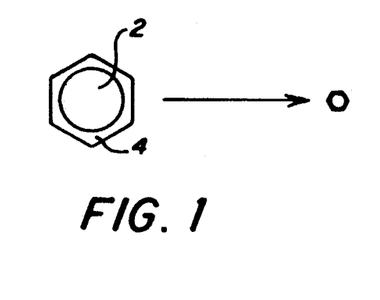
FIG. 1 illustrates the reduction in size of an acid etchable rod inside a hollow inert glass rod.
Figure 2:
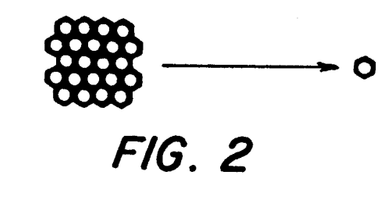
FIG. 2 illustrates stacked rods which have been redrawn several times.
Figure 3:
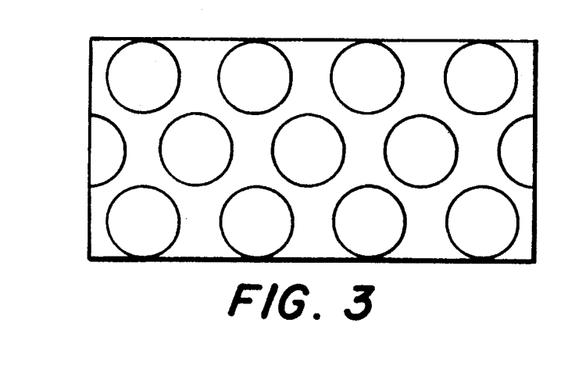
FIG. 3 is a front elevated view of a filter in which the channel glass has been removed.
Figure 4:
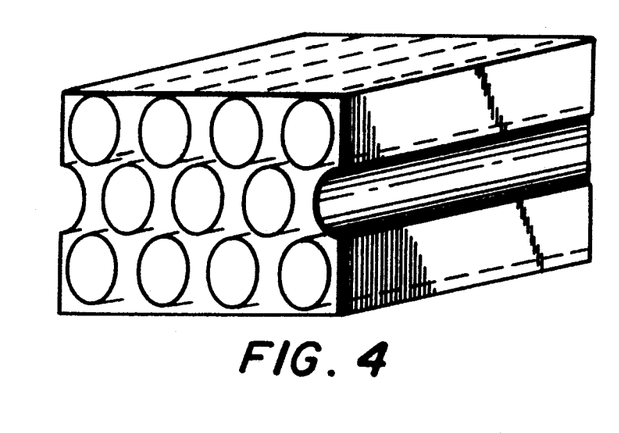
FIG. 4 is a right perspective view of the filter of FIG. 3.
Figure 5:
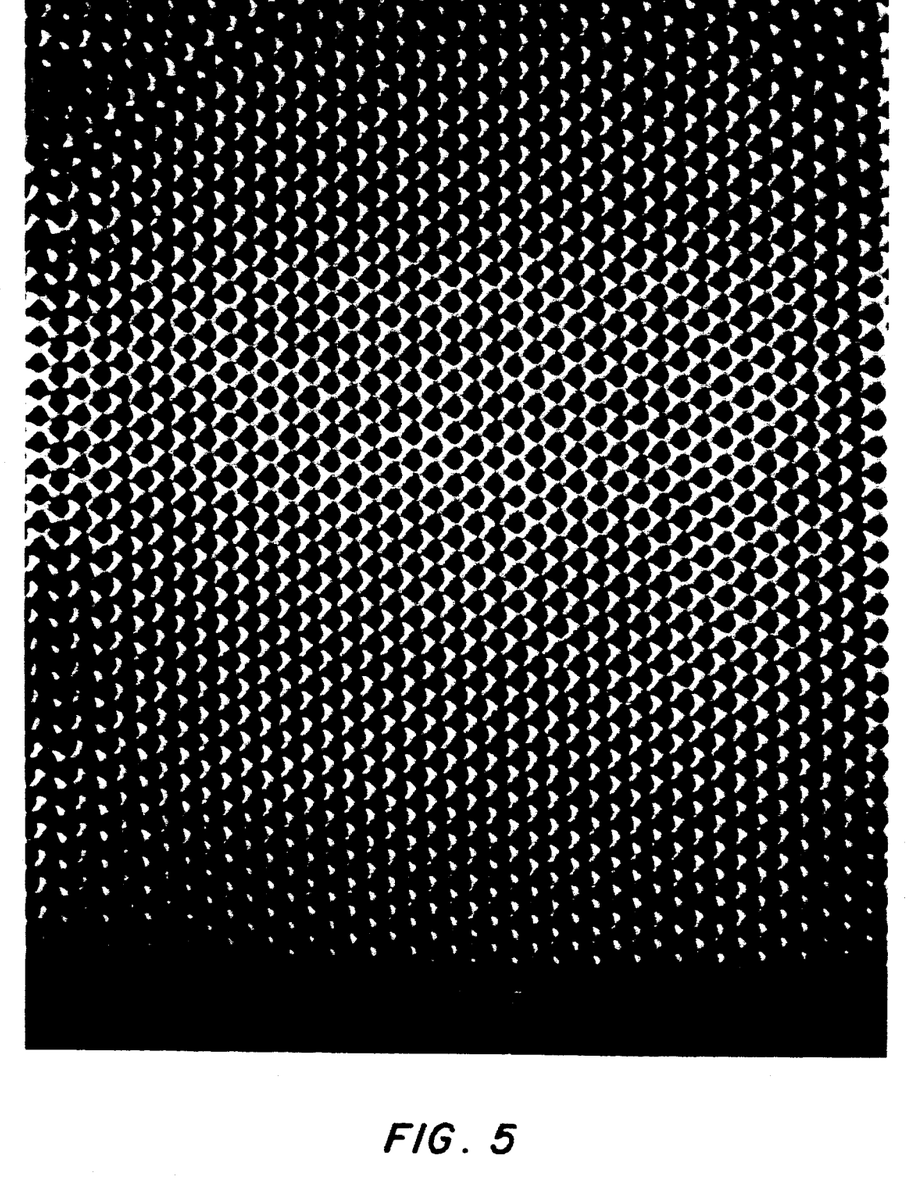
FIG. 5 is a scanning electron micrograph of a filter made according to the present invention having 450 nanometer channel diameters.
Figure 6A:
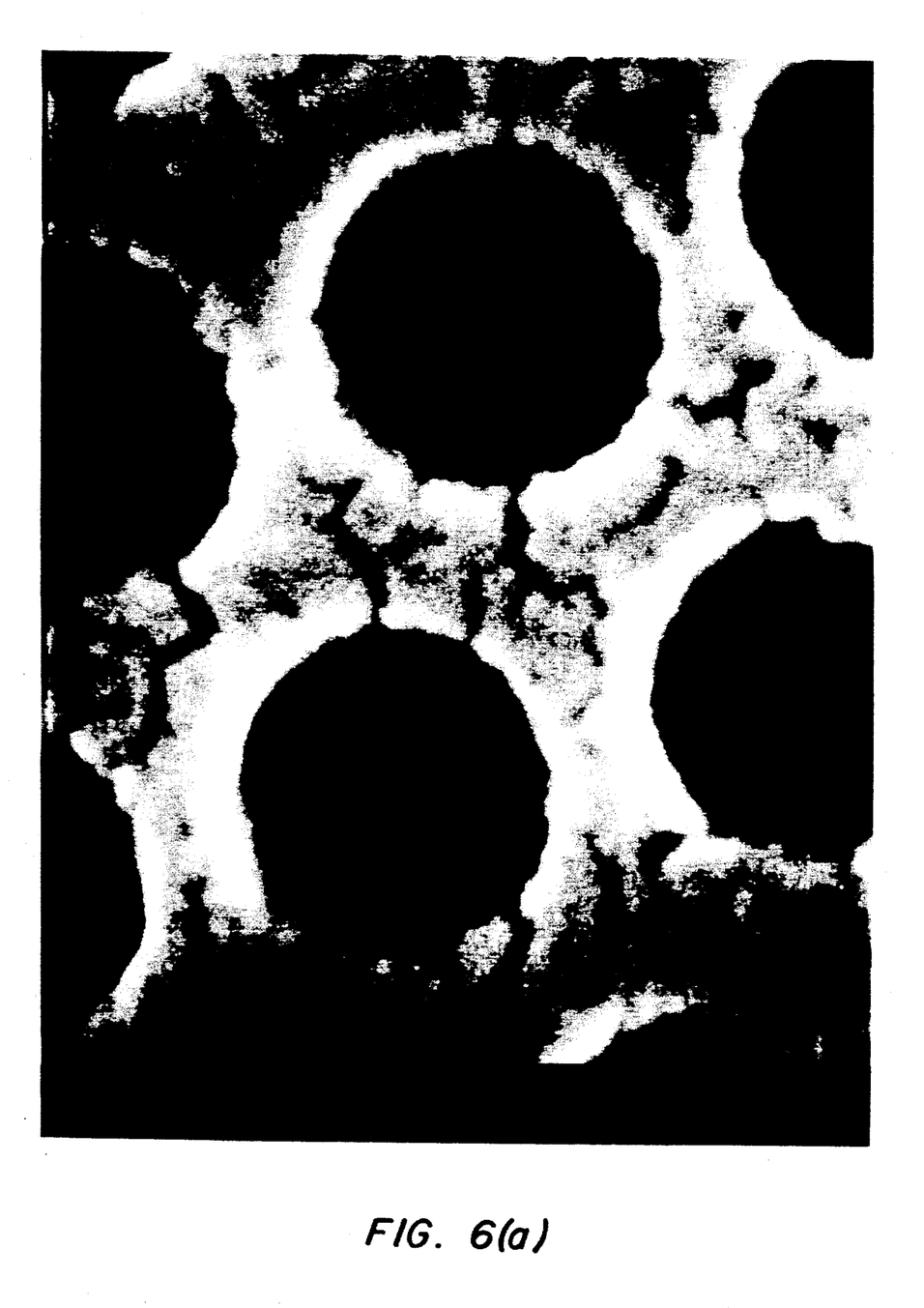
FIG. 6(a) is a scanning electron micrograph of a filter of the present invention having 90 nanometer channel diameters.
Figure 6B:
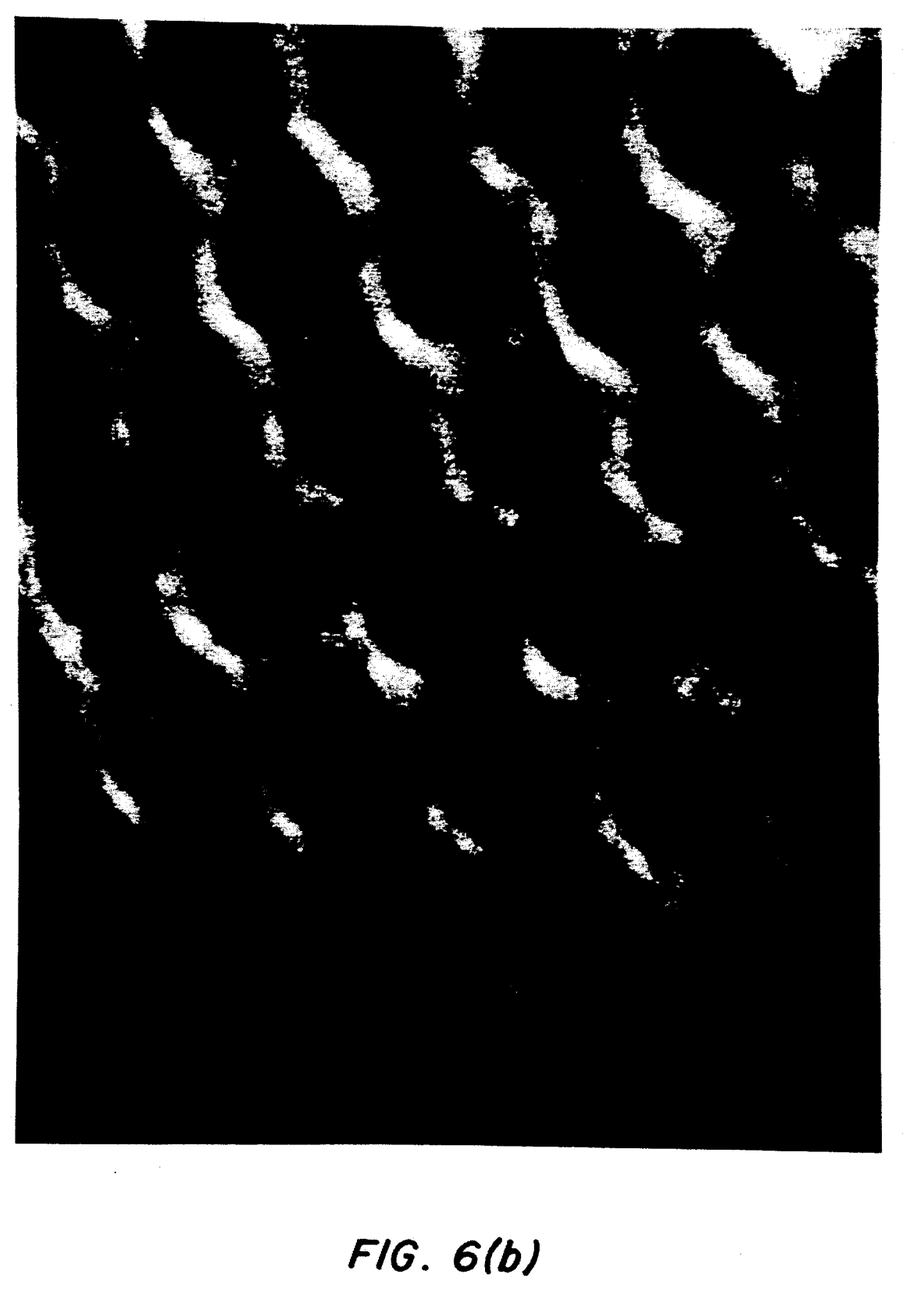
FIG. 6(b) is a scanning electron micrograph of a filter of the present invention having 40 nanometer channel diameters.

The nanochannel filter (NCF) array of the present invention is an arrangement of dissimilar glasses of which at least one glass is usually acid etchable. Although a multitude of configurations are possible, the simplest arrangement is that of a uniform regular array of equally spaced rods of an acid etchable glass imbedded in a matrix of inert glass, in a hexagonal 2-dimensional close packing arrangement. The hexagonal close packing arrangement of hexagonal glass fibers, with acid etchable channels of greater than 1 micron is a well known technology and is frequently used in the first processing step of microchannel plate device fabrication. As is shown in FIG. 1, fabrication starts by insertion of a cylindrical acid etchable glass rod 2, the channel glass, into an inert hexagonal glass tube 4, the matrix glass, whose inner dimensions match that of the rod. The pair is then fused by heating the glasses close to the melting point. The pair is then drawn to reduce the overall cross-section to that of a fine filament. The filaments are then stacked, fused again and redrawn under vacuum, as is shown in FIG. 2. This process is continued until appropriate channel diameters and the desired number of array elements are achieved. Annealing of the glasses is necessary if the glasses chosen are susceptible to work hardening. By adjusting the ratio of the diameter of the etchable glass rod to that of the outside dimension of the hexagonal inert glass tubing, the center to center spacing of the rods and their diameters in the finished product become independently adjustable parameters. A section of the final product is shown in FIGS. 3 and 4. FIG. 5 shows a scanning electron micrograph (SEM) of a hexagonal close packing (HCP) arrangement of channel glasses in relief after acid etching. The sample contains approximately $5 \times 10^6$ channels arranged in a highly regular two dimensional array. The channels are extremely uniform in size throughout the entire area of the array with a diameter of approximately 450 nanometers and the center to center spacing is approximately 750 nanometers. FIG. 6 (a) shows a similar SEM micrograph with 90 nanometer channel diameters. The rough appearance of the channel boundaries and apparent cracking of the surface is due to the approximately 8 nanometer thick incomplete layer of gold deposited on the nanochannel filter surface to avoid charging effects during SEM analysis and is not indicative of the nanochannel filter itself. FIG. 6(b) shows a similiar SEM micrograph with 40 nanometer channel diameters.

Figure 7:
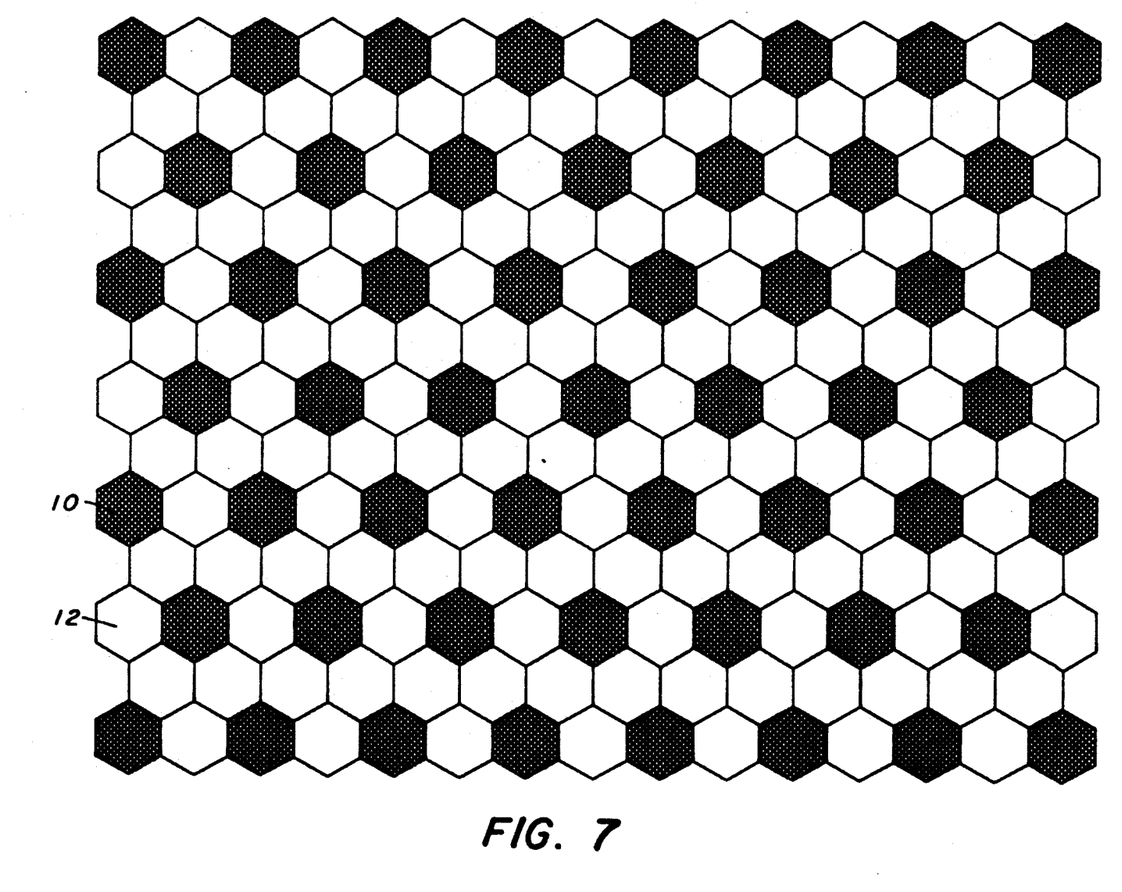
FIG. 7 is a top plan view of a nanochannel glass filter of the present invention composed of solid homogeneous hexagonal rods of either etchable or inert glass.

In another embodiment of the nanochannel glass filter, an array is composed of solid homogeneous hexagonal rods of either etchable or inert glass. An example of such a glass filter is illustrated in FIG. 7. The dark regions are composed of acid etchable pixels or rods 10 and the light regions are composed of inert pixels or rods 12. Squares, slabs and other structures can be inserted into the matrix if the physical properties (melting point, viscosity at working temperatures, thermal expansion coefficient, etc.) of the inserted glass are chosen properly. Many other, more complex and intricate patterns are possible during the nanochannel glass matrix fabrication process.

Figure 8A:
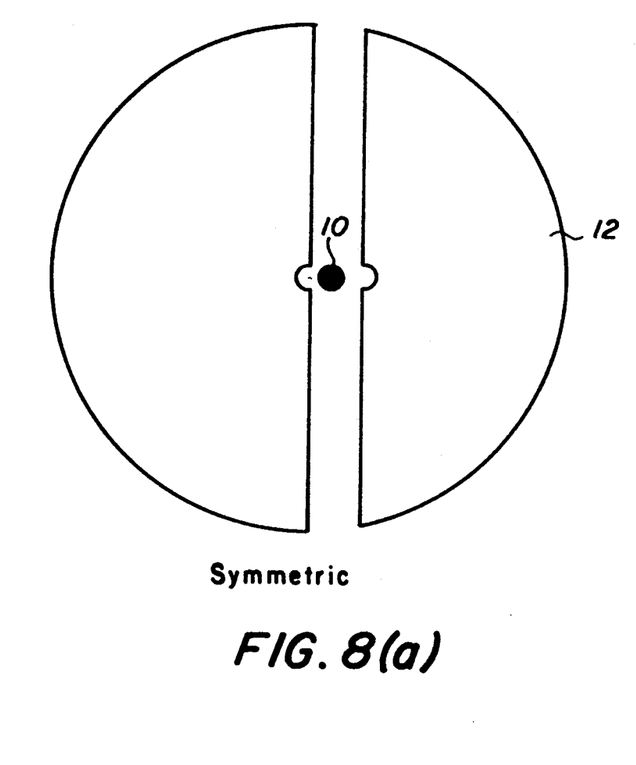
FIG. 8(a) is an alternate embodiment showing the use of solid rods of inert and/or acid-etchable glasses in a split D configuration.
Figure 8B:
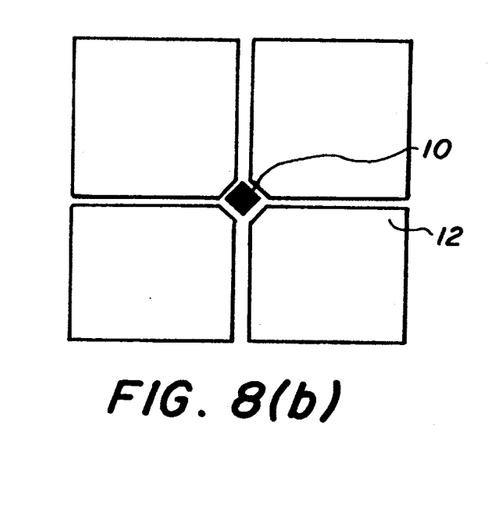
FIG. 8(b) is an alternate embodiment showing the use of solid rods of inert and/or acid-etchable glasses in a square configuration.
Figure 8C:
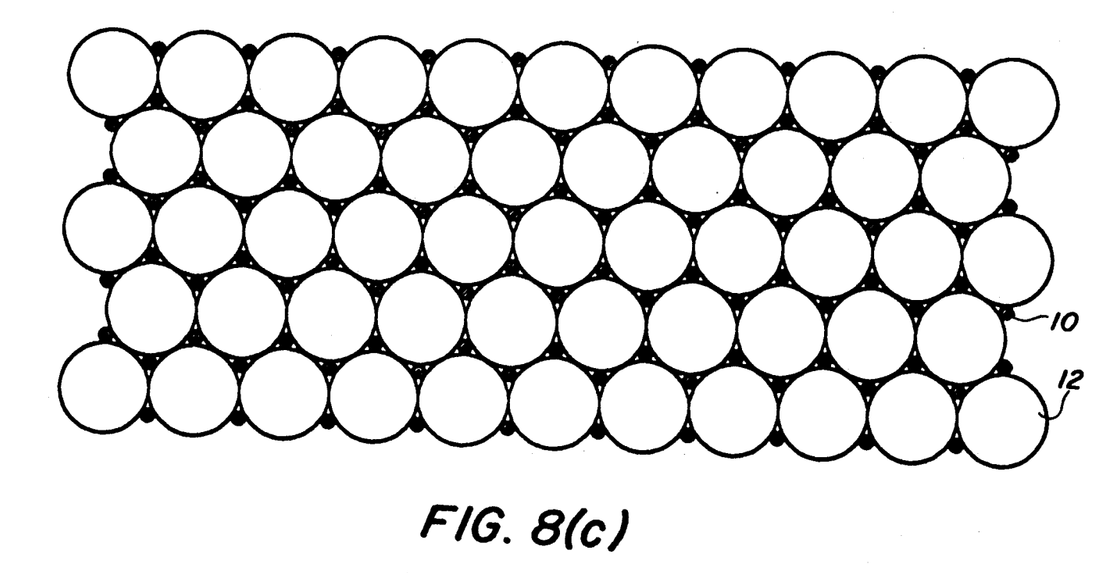
FIG. 8(c) is an alternate embodiment showing the use of solid rods of different sizes wherein the rods are either inert or acid-etchable.

FIGS. 8(a), 8(b), and 8(c) illustrate alternate embodiments of fabricating nanochannel glass. In one of these embodiments, fabrication of nanochannel glass includes the step of extruding a d-shaped rod with a small groove along the center of the flat face, as shown on FIG. 8(a). For tighter tolerances, the groove may be cut instead of being formed by the die used in the extrusion to make the d-shaped rod. An acid-etchable glass fiber or rod drawn down to 100 microns in diameter or smaller is placed in the groove of the d-shaped rod and another d-shaped rod is attached. The rods are stacked for drawing sequences as already described. Nanometer dimensions of the channel diameters can now be accomplished in just two additional draws, minimizing the interdiffusion of the glass types. Extremely smooth high definition channel walls can be fabricated in this fashion. The matrix glass chosen for the d-shaped rod must have a lower working temperature than the etchable fiber so the matrix can flow and close the area around the fiber during the vacuum drawing process without fiber distortion. In practice, a hexagonal rod is used since it has a closed packing geometry. As earlier, dark regions are composed of acid-etchable pixels or rods 10 and the light regions are composed of inert pixels or glass rods 12. In another embodiment, the fabrication method utilizes the radius of the corners of long glass bars with rectangular or square cross-sections. FIG. 8(b) illustrates the square embodiment with dark regions composed of acid-etchable pixels or rods 10 and light regions composed of inert pixels or glass rods 12. The edges can be ground for greater accuracy. The assembly is clamped and drawn under vacuum to produce a fine square filament. The filaments can be restacked and redrawn or combined with other materials in a predetermined complex pattern. As before, channel diameters with nanometer dimensions can be fabricated in just two draws, thus greatly reducing the time the dissimilar glasses are in contact at elevated temperatures. Any other close packing geometry of glass bars, such as triangular, hexagonal, etc., can also be used. In still another embodiment, illustrated in FIG. 8(c), nanochannel glass is fabricated using solid bars 10 of acid-etchable glass in between much larger rods 12 of inert glass.

The fabrication processes are very suitable to mass production requirements. The wafer-like nanochannel filter is generally only a few millimeters thick and is sectioned from a fused matrix bar several feet long. The fused matrix bar is cut from a longer matrix bar which continuously flows from the final drawing process. Up to 100 feet of identical fused matrix bar can be fabricated in a single run, from which more than 50,000 identical nanochannel filters can be cut. In order to produce a filter which can withstand the acid etching treatment, after the wafer-like filter has been cut from the fused stack of fibers, the filter should be annealed at an elevated temperature, preferably about 425° C. for about 2 hours in order to relieve stress in the matrix.

By adjusting the geometry of the outer wall of the tubing so that it has a square, rectangular, triangular, etc. cross-section, the packing arrangement or geometry of the array can be adjusted. Also, by adjusting the shape of the circumference of the channel glass, the channel shape can be altered. More intricate patterns can be fabricated by stacking dissimilar filaments next to each other. The fabrication process for the nanochannel filter array of the present invention yields extremely regular channels whose diameters are adjustable in size from microns to several nanometers.

When a thin section of the nanochannel filter is acid etched completely through, it becomes an excellent filter for sizing small particles suspended in a solution. A backing may be attached to the nanochannel filter for support or the nanochannel filter can be fabricated with a taper for additional strength. Particle separation by size can be accomplished by placing a solution, in which the particles are in suspension, above the filter. As the solution passes through the filter by suction from below the filter and/or by additional pressure above the solution, particles smaller than the channel diameter will pass through the filter. Particles larger than the channel will not pass and remain behind. Mild mixing of the solution above the filter should keep channels free and clear of the larger particles.

In order to allow for etching of channels as small as those used in the present invention, the difference between the relative etch rates of the etchable glass and the inert glass needs to be very large. While in glass filters having larger pore sizes, the etch rate of the etchable glass is 1,000 to 10,000 times the etch rate of the inert glass, in the present invention, the etch rate of the etchable glass is preferably $10^5$ to $10^7$ the etch rate of the inert glass. Because of the microscopic size of the channels formed in the filter, it is also important that the two glasses not diffuse into each other while they are drawn. Therefore, a minimum of heat should be used while the glasses are being drawn. Although the exact drawing temperature is dependent on the glasses used, the drawing temperature is generally between 625° and 750° C. A preferred inert glass is Corning Glass 0120, 8161 or 0080. Corning Glass 0120 is a potash soda lead glass. Preferred etchable glasses are EG-1, EG-2 and EG-4 manufactured by Detector Technology. Using Corning Glass 0120 as the inert glass and EG-2 as the etchable glass, filters have been prepared having average channel diameters of less than 400 Å, preferably less than 100 Å.

Preferably, although acids such as nitric acid and hydrochloric acid can be used to etch the acid etchable glass, the acid used in the acid etching of the etchable glass is preferably an organic acid such as acetic acid which does not leave a residue on the acid inert glass. Preferably, the acid etching solution is at a concentration of about 0.1 to 2%.

The nanochannel filter of the present invention is a complex glass structure of bulk proportions containing about $10^7$ unidirectional hollow channels. The most unique properties of the nanochannel filter of the invention is the very small size of the channels, the accuracy and precision to which these small channels can be arranged form very large and complex structures and the high packing density of the channels. Channel packing densities can approach $10^{12}/cm^2$. Regular arrays can be fabricated with extremely good geometric uniformity and very low variance in channel dimensions. The nanochannels can exceed several millimeters in length. In addition, the channel depth can be varied independently from both the channel diameter and the distance between channels during the fabrication process.

The nanochannel filter array channels of the present invention can be precisely fabricated such that extreme regularity and straightness is maintained over the entire array with very low variance in diameter or geometric spacing. The nanochannel array particle sizing filter has an extremely sharp size cutoff of particles passing through the filter (conservatively, at least an order of magnitude better than membrane filters) and a recovery rate of nearly 100% of all starting materials. This enables the thickness of the filter to be extremely short, greatly reducing retention times. The filter exhibits no compaction at high pressure and may be operated at temperatures in excess of 550° C. The void spacing as a percent of cross-sectional area for a typical hexagonal close packed nanochannel filter array is approximately 40% which allows extremely high flow rates of material through the channels. The straightness of the channels minimizes the dispersion of material passing through the channels once entered and is the most efficient configuration for passage after size separation. For pressure assisted filtering, the channels always remain parallel to the pressure gradient, maximizing material flow. The nanochannel filter glass is generally transparent to visible light, allowing real time monitoring during filtration.

The nanochannel filter may be used in a variety of filtering configurations. These include all differential migration techniques such as chromatography, molecular adsorption and electrophoresis. The channels themselves can be made straight or curved, filled with material or with a chemical lining on the walls, or left as hollow tubes.

Liquids that have different wetting characteristics to the nanochannel filter glass may be separated very efficiently. The liquid that wets the glass most highly would pass through the channels more readily, leaving residual materials behind. Nanochannel filter channels can be fabricated such that the channels can exceed several millimeters in length.

Gases of different molecular weights or diameters can be separated with a pressure gradient $\Delta P$, across the nanochannel filter. The ratio of the average rates of flow $R_1/R_2$, of two different molecular species through an aperture (channel) is proportional to the inverse square root of the ratio of their masses. The smaller or lower molecular weight gases will migrate through the channels faster on the average and hence be fractionated. Since all the channel paths are identical, all material passing through the channels undergo the exact same pressure differentials and interactions with the walls, minimizing the length of the filter required. Precision polymer gas filters available today have maximum operating temperatures of approximately 150° C.

Gasses dissolved in a good wetting liquid may also be separated by combining the above processes.

Adsorption chromatography is the separation of chemical substances by partitioning them between two media according to their chemical adsorption characteristics. This differential migration of particles as they pass through the filter provides a means for separating compounds that are very similar, and would therefore be difficult or impossible to analyze by other methods. Particles that are sensitive to adsorption or electrostatic interactions may be filtered by placing a thin resin or polymer film on the walls of the nanochannel filter channels. Retardation of particles as they pass through the channels, form their interactions with the walls, would allow for the separation of similarly sized particles of different chemical species to be separated. The extremely large surface area to volume ratio of the channels, in conjunction with the extreme uniformity of the channels, permits excellent resolution per unit length compared to porous glass or gel filter columns. This greatly reduces filtering times from current chromatographic techniques with extremely short channel filter lengths. Analytical characterization is accomplished by monitoring the retention time of the different chemical species in the channel. Biological separations and characterizations are also amenable to this type of filtration.

Generally speaking, wafer-like structures, such as nanochannel filters described herein, have a thickness of less than 1 mm, preferably 1–500 microns, and especially 10–200 microns. In a particle sizing filter, thickness may be on the order of a couple of microns to a nanometer. In special applications, such as in chromatography, thickness of the filters may be on the order of tens of centimeters. As already mentioned above, the nanochannel filters are made of glass. Glass is generally defined as an amorphous or noncrystalline material that has a disordered atomic structure which is "frozen" in its disordered arrangement when molten glass is quenched rapidly to a lower temperature. Glass is considered to be a rigid liquid. The channel diameters have been described to be less than 400 angstroms, preferably less than 100 angstroms. They can be as small as about 10–50, prefably 20–40 angstroms.

The formation of the nanochannel glass filter will now be described by way of examples.

EXAMPLE I

The inert glass used was a hexagonal tube of Corning 0120 glass. The etchable glass used was Detector Technology's EG-2. Typical starting dimensions of the glasses were a rod outer diameter of about 1.5 inches and a tube outer diameter of about 2 inches, with inner diameter of the tube matching the outer diameter of the rod. The glasses were fused under vacuum during the drawing process at a temperature of 625° to 750° C. and were drawn down to fine filaments of 0.01 to 0.2 inches (0.03 to 0.5 cm) and cut to lengths of 1 to 3 feet (30 to 90 cm). The filaments were stacked into bundles, approximately 1.5 inches flat to flat, drawn and restacked and redrawn until the desired channel diameter was achieved. Just before the final draw, a cladding is added for strength and to facilitate handling by placing the bundle inside a hollow tube (usual Corning 0120 glass) and drawing under vacuum. To relieve the stress, the glass composition was annealed after each draw. The glass was then cut to the desired length, polished and etched in a weak acid such as 1% HCl, $HNO_3$ or acetic acid to remove the channel glass and leave behind the porous matrix glass and cladding.

EXAMPLE II

Hexagonal monofilaments of Corning 0120 glass and Detector Technology's EG-2 were used as the inert glass and etchable glass filaments, respectively. The monofilaments, typically 0.01 to 0.1 inches (0.025 to 0.25 cm) in width were stacked in predetermined pattern which can be used to make arrays. After the monofilaments are stacked, the process is essentially the same as described in Example I. An advantage to using this technique is that one less draw is required in which the dissimilar filaments are in contact with each other at elevated temperatures, greatly reducing the diffusion of glasses into one another and yielding a stronger matrix as well as finer resolution, especially at glass dimensions around 10 nanometers. Another advantage is that individual pixel replacement is possible with a variety of glass types making very complex structures possible.

What is claimed is:

1. A method for forming a filter comprising the steps of:
   inserting acid etchable glass rods into respective inert hollow glass tubes;
   heating said rods and tubes to fuse each respective rod to a respective tube;
   drawing each of said fused rods and tubes to reduce the diameter of the rods and tubes to thereby form a filament;
   stacking a plurality of said filaments together to form a stack of filaments;
   heating the stack of filaments to fuse the filaments together to form an elongated bar having a plurality of channels filled with etchable glass;
   drawing said bar until each of the channels has a diameter of less than 1 micron;
   cutting the elongated bar to form a wafer-like filter;
   annealing the filter at an elevated temperature; and
   acid etching the etchable glass in the wafer-like filter to form channels therethrough having an average diameter of less than about 1 micron.

2. A method according to claim 1, wherein the tubes are hexagonal in cross-section and the matrix has a hexagonal close-packed configuration.

3. A method according to claim 1, wherein the etchable glass has a rate of etching $10^5$ to $10^7$ as great as the rate of etching of the inert glass.

4. A glass filter made according to the method of claim 1.

5. A method for forming a filter comprising the steps of:
   stacking acid etchable glass filaments with acid inert glass filaments to form a stack of filaments having an oriented array of acid etchable glass filaments;
   heating the stack of filaments to fuse the filaments together to form an elongated bar having a plurality of channels filled with etchable glass;
   drawing said bar until each of the channels has a diameter of less than 1 micron;
   cutting the elongated bar to form a wafer-like filter;
   annealing the filter at an elevated temperature; and
   acid etching the etchable glass in the wafer-like filter to form channels therethrough having an average diameter of less than about 1 micron.

6. A method according to claim 5, wherein said filaments are hexagonal in cross-section and the filter has a hexagonal close-packed configuration.

7. A method according to claim 5, wherein the etchable glass has a rate of etching $10^5$ to $10^7$ as great as the rate of etching of the inert glass.

8. A glass filter made according to the method of claim 1.

9. A method according to claim 5, wherein said filaments are selected from round, aquare, and semicircular cross-sectional shapes and said filter has a configuration selected from hexagonal and aquare close packed configurations.

10. A method according to claim 5, wherein the etchable glass has a rate of etching $10^5$ to $10^7$ as great as the rate of etching of the inert glass.

11. A glass filter made according to the method of claim 5.

* * * * *